(12) United States Patent
Kawaratani et al.

(10) Patent No.: US 8,658,142 B2
(45) Date of Patent: *Feb. 25, 2014

(54) COSMETIC COMPOSITIONS HAVING LONG LASTING SHINE

(75) Inventors: Yoriko Kawaratani, Chuou-ku (JP); Hy Si Bui, Piscataway, NJ (US)

(73) Assignee: L'Oreal, Paris (FR)

( * ) Notice: Subject to any disclaimer, the term of this patent is extended or adjusted under 35 U.S.C. 154(b) by 118 days.

This patent is subject to a terminal disclaimer.

(21) Appl. No.: 13/110,597

(22) Filed: May 18, 2011

(65) Prior Publication Data

US 2012/0294815 A1 Nov. 22, 2012

(51) Int. Cl.
*A61K 8/72* (2006.01)
*A61Q 1/06* (2006.01)
*A61K 31/765* (2006.01)

(52) U.S. Cl.
USPC .......................................... 424/64; 424/78.03

(58) Field of Classification Search
USPC .......................................................... 424/64
See application file for complete search history.

(56) References Cited

U.S. PATENT DOCUMENTS

| | | | |
|---|---|---|---|
| 3,937,811 | A | 2/1976 | Papantoniou et al. |
| RE29,871 | E | 12/1978 | Papantoniou et al. |
| 6,491,927 | B1 | 12/2002 | Arnaud et al. |
| 6,517,818 | B1 | 2/2003 | Golz-Berner et al. |
| 7,314,904 | B2 * | 1/2008 | Nadolsky et al. ........... 526/307.5 |
| 7,423,104 | B2 | 9/2008 | Lion |
| 2002/0004054 | A1 | 1/2002 | Callelo et al. |
| 2003/0067545 | A1 | 4/2003 | Giron et al. |
| 2004/0170586 | A1 | 9/2004 | Ferrari |
| 2005/0220728 | A1 | 10/2005 | Kanji et al. |
| 2007/0258932 | A1 | 11/2007 | Bui et al. |
| 2008/0102049 | A1 * | 5/2008 | McDermott ........................ 424/64 |
| 2008/0152607 | A1 | 6/2008 | Malle et al. |
| 2008/0207871 | A1 | 8/2008 | Seiler |
| 2008/0286152 | A1 | 11/2008 | Schmidt |
| 2008/0317693 | A1 | 12/2008 | Ricard et al. |
| 2009/0162303 | A1 * | 6/2009 | Barba et al. ...................... 424/61 |

FOREIGN PATENT DOCUMENTS

| | | | | |
|---|---|---|---|---|
| EP | 955039 | | 11/1999 | |
| EP | 1870082 | | 12/2007 | |
| FR | 2232303 | | 1/1975 | |
| FR | 2829344 | | 3/2003 | |
| WO | WO00/59456 | * | 10/2000 | .................... 424/401 |
| WO | WO 2004/055081 | | 7/2004 | |

OTHER PUBLICATIONS

"Regalite TM R1100 Hydrocarbon Resin" Product Data Sheet by Eastman. Accessed online at www.eastman.com on Feb. 11, 2013.*
U.S. Appl. No. 13/110,597, filed May 18, 2011, Kawaratani et al.
U.S. Appl. No. 13/110,599, filed May 18, 2011, Kawaratani et al.
U.S. Appl. No. 13/110,602, filed May 18, 2011, Kawaratani et al.
U.S. Appl. No. 13/110,609, filed May 18, 2011, Bouchra Bouarfa.
International Cosmetic Ingredient Dictionary and Handbook (9th ed. 2002), published by the CTFA, 1101 17th Street, N.W, Suite 300, Washington, DC 20036-4702.
Amendment filed in U.S. Appl. No. 13/110,602 on Nov. 18, 2013.

* cited by examiner

*Primary Examiner* — Janet Epps-Smith
*Assistant Examiner* — Audrea Buckley
(74) *Attorney, Agent, or Firm* — L'Oreal USA

(57) ABSTRACT

The invention relates to a cosmetic composition comprising at least one polyester that may be obtained by reacting:
- a tetraol containing from 4 to 10 carbon atoms;
- a linear or branched saturated monocarboxylic acid containing from 9 to 23 carbon atoms;
- a cyclic dicarboxylic acid containing from 6 to 12 carbon atoms; and
- an aromatic monocarboxylic acid containing from 7 to 11 carbon atoms;

at least one resin chosen from hydrocarbon-based resins; at least one hyperbranched polyol compound; at least one nonvolatile solvent chosen from monoalcohols; at least one co-solvent chosen from esters; at least one nonvolatile silicone oil; optionally, at least one wax; and optionally, at least one colorant, as well as to methods of using such compositions.

42 Claims, No Drawings

COSMETIC COMPOSITIONS HAVING LONG LASTING SHINE

BACKGROUND OF THE INVENTION

Cosmetic compositions used to make up or enhance the appearance of keratinous substrates such as skin, lips, hair and eyelashes are oftentimes required to be able to impart various properties such as high shine or gloss and long lasting shine, as well as long wear. However, the formulation of cosmetic products that can deliver all these properties at the same time can pose some challenges. For example, cosmetic compositions using traditional ingredients known to impart shine or gloss, such as oils, have very poor transfer resistance and wear properties. In order to overcome these problems, film forming resins such as silicone film forming resins are generally employed to improve the transfer resistance and wear of cosmetic compositions. While the use of silicone film forming resins in cosmetics is popular, one drawback associated with their use is that they tend to be brittle and flake off. This phenomenon results in the need to use a plasticizer, in combination with the resin, in order to render the resultant film more flexible and, hence, less susceptible to flake off and poor transfer resistance. Moreover, the resultant films formed by the resins are not glossy, are uncomfortable on human skin and, at times, have a tacky feel.

Another way to achieve high shine and long lasting shine properties is by increasing the levels of shine-enhancing agents without resorting to the use of silicones, thereby, creating silicone-free formulations which are desired by consumers. However, such compositions tend to be very heavy and tacky, thereby, causing discomfort upon application.

Alternatively, two step products have been developed, using a topcoat to provide shine and/or comfort to a basecoat which is matte and/or dry in an effort to provide good wear of color and shine at the same time. However, this presents the drawback of having to formulate two different compositions and to the consumer who has to employ two separate products.

Thus, it is an object of the present invention to provide a method and composition for making up or enhancing the appearance of skin or hair in a manner which delivers a combination of long wear, high shine and long lasting shine properties, as well as a non-tacky feel, comfort and desirable texture characteristics upon application onto skin. At the same time, it is desirable that cosmetic compositions, particularly, lipstick compositions, have minimal feathering and migration disadvantages.

SUMMARY OF THE INVENTION

The present invention relates to cosmetic compositions containing:
(a) at least one polyester obtained by reacting:
   a tetraol containing from 4 to 10 carbon atoms;
   a linear or branched saturated monocarboxylic acid containing from 9 to 23 carbon atoms;
   a cyclic dicarboxylic acid containing from 6 to 12 carbon atoms; and
   an aromatic monocarboxylic acid containing from 7 to 11 carbon atoms;
(b) at least one resin chosen from hydrocarbon-based resins;
(c) at least one hyperbranched polyol compound;
(d) at least one non-volatile solvent chosen from monoalcohols;
(e) at least one co-solvent chosen from esters;
(f) at least one nonvolatile silicone oil;
(g) optionally, at least one wax; and
(h) optionally, at least one colorant,
wherein the content of the silicone oil is less than or equal to 10% by weight based on the total weight of the composition.

According to another aspect of the present invention, there is provided a method of making up a keratinous substrate involving applying onto the keratinous substrate the above-disclosed composition.

It has been surprisingly discovered that the above-described composition provides long wear of color and long-lasting shine, and/or comfort, good film deposit and texture characteristics as well as a non-tacky and a smooth/creamy feel when applied onto a keratinous substrate. It was also surprisingly discovered that lipstick formulas of the above-described compositions exhibited minimal feathering and migration disadvantages.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" or "film-forming polymer" as used herein means a polymer or resin that leaves a film on the substrate to which it is applied, for example, after a solvent accompanying the film former has evaporated, absorbed into and/or dissipated on the substrate.

The "wear" of compositions as used herein, refers to the extent by which the color of the composition remains the same or substantially the same as at the time of application, as viewed by the naked eye, after a certain period or an extended period of time. Wear properties may be evaluated by any method known in the art for evaluating such properties. For example, wear may be evaluated by a test involving the application of a composition to human hair, skin or lips and evaluating the color of the composition after a specified period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

Depending on the intended application, such as a stick, hardness of the composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is □ 50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on keratin materials. In addition, this hardness may impart good impact strength to the inventive compositions, which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 25° C., 37° C., 45° C. and under freeze-thaw conditions. A composition is considered to lack stability if in any of these tests an abnormality that impedes functioning of the composition is observed. The skilled artisan will readily recognize an abnormality that impedes functioning of a composition based on the intended application.

The cosmetic compositions and methods of the present invention can comprise, consist of, or consist essentially of the essential elements and limitations of the invention described herein, as well as any additional or optional ingredients, components, or limitations described herein or otherwise useful in personal care.

Polyester

The composition according to the invention comprises at least one polyester obtained by reacting a polyol, a polycarboxylic acid, a non-aromatic monocarboxylic acid and an aromatic monocarboxylic acid.

In particular, the at least one polyester for use in the present invention is obtained by reacting:
 a tetraol containing from 4 to 10 carbon atoms;
 a linear or branched saturated monocarboxylic acid containing from 9 to 23 carbon atoms;
 a cyclic dicarboxylic acid containing from 6 to 12 carbon atoms;
 an aromatic monocarboxylic acid containing from 7 to 11 carbon atoms.

Advantageously, the at least one polyester for use in the present invention may be obtained by reacting:
 from 10% to 30% by weight of tetraol containing from 4 to 10 carbon atoms;
 from 40% to 80% by weight of a linear or branched saturated monocarboxylic acid containing from 9 to 23 carbon atoms;
 from 5% to 30% by weight of a cyclic dicarboxylic acid containing from 6 to 12 carbon atoms;
 from 0.1% to 10% by weight of an aromatic monocarboxylic acid containing from 7 to 11 carbon atoms,
the contents being expressed as weight percentages relative to the total weight of the polyester.

The at least one polyester for use in the present invention comprises a tetraol. The term "tetraol" means a polyol comprising 4 hydroxyl groups.

A tetraol used for the preparation of the polyester is advantageously a linear, branched and/or cyclic, saturated or unsaturated hydrocarbon-based compound containing from 4 to 10 carbon atoms, and possibly also comprising one or more oxygen atoms intercalated in the chain (ether function). Obviously, a mixture of such tetraols may be used.

A tetraol may in particular be a saturated, linear or branched hydrocarbon-based compound containing 4 to 10 carbon atoms.

A tetraol may be chosen from pentaerythritol or tetramethylolmethane, erythritol, diglycerol and ditrimethylolpropane.

Preferably, the tetraol is chosen from pentaerythritol and diglycerol.

Even more preferentially, a tetraol may be pentaerythritol.

The content of tetraol, or tetraol mixture, may represent from 10% to 30% by weight, especially from 12% to 25% by weight and better still from 14% to 22% by weight relative to the total weight of the polyester.

The at least one polyester for use in the present invention also comprises a linear or branched, saturated monocarboxylic acid containing from 9 to 23 carbon atoms and especially 12 to 22 carbon atoms.

The term "saturated monocarboxylic acid" means a compound of formula RCOOH in which R is a saturated linear or branched hydrocarbon-based radical containing from 8 to 23 carbon atoms and especially from 11 to 22 carbon atoms. Obviously, a mixture of such monocarboxylic acids may be used.

Among the saturated monocarboxylic acids that may be used, mention may be made, alone or as a mixture, of nonanoic acid, isononanoic acid or pelargonic acid, decanoic acid or capric acid, lauric acid, tridecanoic acid or tridecylic acid, myristic acid, palmitic acid, stearic acid, isostearic acid, arachidic acid and behenic acid.

Preferably, lauric acid, myristic acid, isononanoic acid, nonanoic acid, palmitic acid, isostearic acid, stearic acid or behenic acid, and mixtures thereof, may be used.

Preferentially, isostearic acid or stearic acid is used.

When the saturated monocarboxylic acid is liquid at room temperature, it generally leads to a polyester that is liquid at room temperature.

Liquid monocarboxylic acids that may be mentioned include nonanoic acid, isononanoic acid and isostearic acid.

When the saturated monocarboxylic acid is solid at room temperature, it generally leads to a polyester that is solid at room temperature.

Solid monocarboxylic acids that may be mentioned include decanoic acid, lauric acid, tridecanoic acid, myristic acid, palmitic acid, stearic acid, arachidic acid and behenic acid.

The content of saturated monocarboxylic acid, or the mixture of the said acids, represents from 40% to 80% by weight, especially from 42% to 75% by weight, or even 45% to 70% by weight and better still 50% to 65% by weight relative to the total weight of the polyester.

The at least one polyester for use in the present invention also comprises a cyclic dicarboxylic acid containing from 6 to 12 carbon atoms and especially containing 8 carbon atoms. The cyclic dicarboxylic acid may be aromatic or non-aromatic. The cyclic dicarboxylic acid is preferably aromatic.

Obviously, a mixture of such cyclic dicarboxylic acids may be used.

A cyclic dicarboxylic acid may be chosen from cyclopropanedicarboxylic acid, cyclohexanedicarboxylic acid, cyclobutanedicarboxylic acid, phthalic acid, terephthalic acid, isophthalic acid, tetrahydrophthalic acid, naphthalene-2,3-dicarboxylic acid and naphthalene-2,6-dicarboxylic acid, or mixtures thereof.

Preferably, the cyclic dicarboxylic acid is chosen from phthalic acid, terephthalic acid and isophthalic acid. Phthalic acid may be advantageously used in its anhydride form.

Preferentially, the cyclic dicarboxylic acid is isophthalic acid.

A cyclic dicarboxylic acid, or a mixture of such diacids, may represent from 5% to 30% by weight and preferably from 15% to 25% by weight relative to the total weight of the polyester.

The at least one polyester for use in the present invention also comprises an aromatic monocarboxylic acid containing from 7 to 11 carbon atoms.

The term "aromatic monocarboxylic acid" means a compound of formula R'COOH, in which R' is an aromatic hydrocarbon-based radical containing 6 to 10 carbon atoms; R' is in particular a phenyl radical, optionally substituted with 1 to 3 alkyl radicals containing from 1 to 4 carbon atoms.

A mixture of such aromatic monocarboxylic acids may be used.

The aromatic monocarboxylic acid may be chosen from benzoic acid and 4-tert-butylbenzoic acid.

The aromatic monocarboxylic acid is preferably benzoic acid.

The said aromatic monocarboxylic acid, or the mixture of the said acids, represents from 0.1% to 10% by weight, especially from 0.5% to 9.95% by weight and better still from 1% to 9.5% by weight, or even from 1.5% to 8% by weight relative to the total weight of the polyester.

According to one preferred embodiment, the at least one polyester for use in the present invention is obtained by reacting:

from 12% to 25% by weight of a tetraol containing from 4 to 10 carbon atoms;
from 40% to 75% by weight of a linear or branched saturated monocarboxylic acid containing from 9 to 23 carbon atoms;
from 15% to 25% by weight of a cyclic dicarboxylic acid containing from 6 to 12 carbon atoms;
from 0.5% to 9.95% by weight of an aromatic monocarboxylic acid containing from 7 to 11 carbon atoms, the contents being expressed as weight percentages relative to the total weight of the polyester.

According to another preferred embodiment, the at least one polyester for use in the present invention is obtained by reacting:

from 14% to 22% by weight of a tetraol containing from 4 to 10 carbon atoms;
from 45% to 70% by weight of a linear or branched saturated monocarboxylic acid containing from 9 to 23 carbon atoms;
from 15% to 25% by weight of a cyclic dicarboxylic acid containing from 6 to 12 carbon atoms;
from 1% to 9.5% by weight of an aromatic monocarboxylic acid containing from 7 to 11 carbon atoms,
the contents being expressed as weight percentages relative to the total weight of the polyester.

According to another preferred embodiment, the at least one polyester for use in the present invention is obtained by reacting:

from 14% to 22% by weight of a tetraol containing from 4 to 10 carbon atoms;
from 50% to 65% by weight of a linear or branched, saturated monocarboxylic acid containing from 9 to 23 carbon atoms;
from 15% to 25% by weight of a cyclic dicarboxylic acid containing from 6 to 12 carbon atoms;
from 1.5% to 8% by weight of an aromatic monocarboxylic acid containing from 7 to 11 carbon atoms,
the contents being expressed as weight percentages relative to the total weight of the polyester.

In one preferred embodiment of the at least one polyester for use in the present invention, the aromatic monocarboxylic acid is present in a molar amount of less than or equal to that of the linear or branched saturated monocarboxylic acid; in particular, the ratio between the number of moles of aromatic monocarboxylic acid and the number of moles of linear or branched saturated monocarboxylic acid ranges from 0.08 to 0.70. The said weight ratio preferably ranges between 0.10 and 0.60 and more preferentially from 0.12 to 0.40.

According to one embodiment of the invention, the at least one polyester for use in the present invention may be chosen from benzoic acid/isophthalic acid/isostearic acid/pentaerythritol polyesters and benzoic acid/isophthalic acid/stearic acid/pentaerythritol polyesters, and mixtures thereof.

These monomers are especially used in the monomer concentration ranges described previously.

Preferably, the at least one polyester for use in the present invention has:
- an acid number, expressed as mg of potassium hydroxide per g of polyester, of greater than or equal to 1; especially between 2 and 30 and even better still between 2.5 and 15; and/or
- a hydroxyl number, expressed in mg of potassium hydroxide per g of polyester, of greater than or equal to 40; especially between 40 and 120 and better still between 40 and 80.

These acid and hydroxyl numbers may be readily determined by a person skilled in the art via the usual analytical methods.

Preferably, a polyester of the invention has a weight-average molecular mass (Mw) of between 3000 and 1 000 000 g/mol, or even between 3000 and 300 000 g/mol.

The average molecular weight may be determined by gel permeation chromatography or by light scattering, depending on the solubility of the polymer under consideration.

Preferably, the at least one polyester for use in the present invention has a viscosity, measured at 110° C., of between 20 and 4000 mPa·s, especially between 30 and 3500 mPa·s or even between 40 and 3000 mPa·s and better still between 50 and 2500 mPa·s. This viscosity is measured in the manner described hereinbelow.

According to one preferred embodiment, the at least one polyester for use in the present invention may be in liquid form at room temperature. A liquid polyester may have a weight-average molecular mass (Mw) ranging from 40 000 to 1 000 000 g/mol and preferably ranging from 50 000 to 300 000 g/mol.

A liquid polyester may have a viscosity, measured at 110° C., ranging from 1000 to 4000 mPa·s and preferably ranging from 1500 to 3000 mPa·s.

In particular, a liquid polyester may be a benzoic acid/isophthalic acid/isostearic acid/pentaerythritol polyester, these monomers especially being present in the monomer concentration ranges described previously.

According to another embodiment, the at least one polyester for use in the present invention may also be in solid form at room temperature. A solid polyester may have a weight-average molecular mass (Mw) ranging from 3000 to 30 000 g/mol and preferably ranging from 8000 to 15 000 g/mol.

The solid polyester may have a viscosity, measured at 80° C., ranging from 20 to 1000 mPa·s and preferably ranging from 50 to 600 mPa·s.

In particular, a solid polyester may be a benzoic acid/isophthalic acid/stearic acid/pentaerythritol polyester, these monomers being present especially in the monomer concentration ranges described previously.

The at least one polyester for use in the present invention may be prepared according to the synthetic process described in patent application EP-A-1 870 082.

The viscosity of the at least one polyester for use in the present invention may be measured in the manner described hereinbelow.

The viscosity at 80° C. or at 110° C. of the at least one polyester for use in the present invention is measured using a cone-plate viscometer of Brookfield CAP 1000+ type.

The appropriate cone-plate is determined by a person skilled in the art on the basis of his knowledge; especially:
- between 50 and 500 mPa·s, a 02 cone may be used,
- between 500 and 1000 mPa·s: 03 cone,
- between 1000 and 4000 mPa·s: 05 cone, and
- between 4000 and 10 000 mPa·s: 06 cone.

The at least one polyester for use in the present invention may be readily conveyed in cosmetic oily or solvent media, especially oils, fatty alcohols and/or fatty esters.

The at least one polyester for use in the present invention may be readily prepared, in a single synthetic step, without producing any waste, and at low cost.

The at least one polyester for use in the present invention may advantageously be branched so as to generate a network by interweaving of polymer chains, and thus to obtain the desired properties, especially in terms of improved adhesion or wear and improved gloss, and in terms of solubility.

According to one embodiment, a composition of the invention may comprise at least two polyesters that are different from each other.

Preferred polyesters for use in the present invention are chosen from benzoic acid/isophthalic acid/isostearic acid/pentaerythritol polyesters and benzoic acid/isophthalic acid/stearic acid/pentaerythritol polyesters, and mixtures thereof.

A particularly preferred polyester for use in the present invention is benzoic acid/isophthalic acid/isostearic acid/pentaerythritol polyester available from the supplier Chimex.

The at least one polyester of the present invention is present in a composition in an amount ranging from about 0.5% to about 25% by weight, preferably from about 1% to about 20% by weight, more preferably from about 1.5% to 18% about by weight, or even more preferably from about 2% to about 15% by weight based on the total weight of the composition, including all ranges and subranges within these ranges.

Hydrocarbon-Based Resins

According to the present invention, compositions comprising at least one resin chosen from hydrocarbon-based resins are provided. Such resins are formulated by dissolving them in an appropriate solvent.

The at least one resin chosen from hydrocarbon-based resins of the present disclosure are polyolefins. These polyolefins are generally nonpolar and, at best, only slightly water soluble, if not substantially water insoluble.

In some embodiments, these hydrocarbon-based resins are thermoplastics and often have a low molecular weight. In preferred embodiments, but not in all embodiments, "low molecular weight" means, unless specified otherwise, that the weight average molecular weight of the at least one resin chosen from hydrocarbon-based resins is about 5,000 or less. In another embodiment, the weight average molecular weight is about 2,200 or less. In yet another embodiment, the weight average molecular weight is about 1,000 or less. Of course, a polyolefin that has a slightly higher molecular weight and is a polyolefin that can provide the advantages of the invention is also contemplated by the term "low molecular weight."

The number-average molar masses (Mn) are determined by gel permeation liquid chromatography (THF solvent, calibration curve established with linear polystyrene standards, refractometric detector).

In one embodiment, the at least one resin chosen from hydrocarbon-based resins has a refractive index of less than 1.5 when measured at between 18 and 25 degrees centigrade. In another embodiment, the at least one resin chosen from hydrocarbon-based resins has a refractive index of less than 1.3 when measured at between 18 and 25 degrees centigrade.

The at least one resin chosen from hydrocarbon-based resins includes, without limitation, low molecular weight (MW between approximately 770 and 2200) thermoplastic polyolefins containing C5+olefin, C5+paraffins and/or C5+diolefin monomers. These C5+polyolefins (C5PO) may also be hydrogenated to promote stability. More preferably, these polyolefins are C5-C20 polyolefins, even more preferably, C6-C20 polyolefins, synthesized via thermal or catalytic polymerization of coal-tar fractions, cracked petroleum distillates, terpenes or pure olefinic monomers. Aliphatic feedstreams used to produce these polyolefins are typically composed of C-5 and C-6 paraffins, olefins and diolefins, the main reactive components of which are often piperylenes such as is and trans-1,3-pentadiene. Substituted C-5 and C-6 olefins are often used as feedstreams was well.

C5PO may be found in a number of commercial products including, without limitation, those sold by Eastman Chemical Company under the trademark Eastotac® and Piccotac® resins. In one embodiment, the C5PO used is a low molecular weight thermoplastic polymer having a refractive index of less than 1.5. In another embodiment, this C5PO has a refractive index of less than 1.3. Both Eastotac® and Piccotac® resins can be made from monomers such as trans-1,3-pentadiene, C-15-1,3-pentadiene,2-mthyl-2-butene, dicyclopentadiene, cyclopentadiene and cyclopentene monomers. Eastotac® resins are usually hydrogenated during manufacture of the resulting resins while the Piccotac® resins are generally not.

Also useful as polyolefins in accordance with the present invention are Piccolyte® polyterpene hydrocarbon resins such as Piccolyte® A115, which is a polymer of alpha-pinene [CAS Reg. No. 31393-98-3] available from Hercules Inc. Resin Division, Hercules Plaza, 1313 North Market Street, Wilmington Del. 19894-0001.

In yet another embodiment, the at least one resin chosen from hydrocarbon-based resins includes, without limitation, low molecular weight, lightly colored, inert thermoplastic resins derived from petrochemical feedstocks. Preferably, these thermoplastic polymers are also partially or fully hydrogenated. Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp. Other examples include certain hydrogenated polycyclopentadienes and hydrogenated styrene/methylstyrene/indene copolymers sold under the trade name Regalite®. Some of the Regalites are made from C 8+monomers which include, without limitation, vinyl toluene, dicyclopentadiene, indene, alpha-methyl styrene, styrene and methyl indene. These low molecular weight hydrocarbon resins may be found in a number of commercial products including without limitation those sold by Eastman Chemical Middelburg BV, Tobias Asserlaan 5, 2517 KC Den Haag, the Netherlands, under the trademarks Regalite®, Eastotac® and Piccotac®. A material that typifies a hydrocarbon resin that may be used in accordance with the present invention is Regalite® R1090 hydrogenated thermoplastic resin. Other useful polyolefins of this type include Regalite® R1125, R1100, R9100, R7100, R81010 and R81100.

Any of the polyolefin materials used herein may further include conventional additives known in the plastics industry. For example, Regalite® R1090 hydrocarbon resin is stabilized with tetrakis [methylene(3,5-di-tert-butyl-4-hydroxyhydrocinnamate)]methane antioxidant.

Other examples of the at least one resin chosen from hydrocarbon-based resins are:

aliphatic pentanediene resins such as those derived from the majority polymerization of the 1,3-pentanediene (trans or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500. Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentadiene dimers such as those derived from the polymerization of first monomers chosen from indene and styrene, and of second monomers chosen from cyclopentadiene dimers such as dicyclopentadiene, methyldicyclopentadiene and other pentanediene dimers, and mixtures thereof. These resins generally have a molecular weight ranging from 500 to 800, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from .alpha.-pinene, .beta.-pinene and limonene, and mixtures thereof. These resins may have a molecular weight ranging from 300 to 2000. Such resins are sold, for example, under the names Piccolyte A115 and S125 by the company Hercules, and Zonarez 7100 or Zonatac 105 Lite by the company Arizona Chem.

Mention may also be made of certain modified resins such as hydrogenated resins, for instance those sold under the name. Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

In another embodiment of the invention, the hydrocarbon-based resins used, irrespective of their refractive index, are polyolefins that do not include appreciable amounts (greater than about 5 percent by weight) of alkylated polyvinyl pyrrolidone monomers, polyvinylpyrrolidone monomers or monoalkyl esters of poly(methylvinylether/maleic acid) as disclosed in U.S. Patent Application Publication No. 2002/0004054, published Jan. 10, 2002, naming Callelo et al. (see 0118-0122). In one embodiment, those hydrocarbon-based resins have a refractive index of less than 1.5.

Particularly preferred resins chosen from hydrocarbon-based resins for use in the present invention are chosen from indene hydrocarbon-based resins, in particular, the hydrogenated indene/methylstyrene/styrene copolymers sold under the trade name "Regalite®" by the company Eastman Chemical, such as, for example, Regalite® R1100, Regalite®

R1090, Regalite® R7100, Regalite® R1010 Hydrocarbon Resin and Regalite® R1125 Hydrocarbon Resin.

Other particularly preferred resins chosen from hydrocarbon-based resins for use in the present invention are chosen from thermoplastic polyolefins containing C5+olefin, C5+paraffins and/or C5+diolefin monomers, in particular, C5+polyolefins (C5PO) sold under the tradenames Eastotac® and Piccotac® resins sold by Eastman Chemical Company.

The amount of the at least one resin chosen from hydrocarbon-based resins will depend on a number of factors including, without limitation, the polyolefins or mixture of polyolefins selected, their desired concentration, the solvent or solvent mixture, solubility, the nature of any other components that may be added to the film former or which will interact with the film former once formulated into a cosmetic or personal care composition, the process conditions such as temperature that will be used and the like.

In addition to contributing to improved shine, the hydrocarbon-based resins of the present invention are often characterized by being generally water insoluble and/or offering excellent adherence to the skin. These resins may preferably be formulated by dissolving, dispersing, solubilizing, emulsifying, etc. the hydrocarbon-based resins, such as C5PO, in a hydrocarbon solvent. Hydrocarbon solvents are preferred and useful hydrocarbon solvents in the practice of the invention include, but are not limited to, mineral oils, mineral solvents, mineral spirits, petroleum, petrolatum, waxes, synthetic hydrocarbons, animal oils, vegetable oils, and mixtures of various hydrogen carbons. Water and other aqueous solvents may also be possible for certain formulations in which case a solubilizer or emulsifier may also be desirable. In an embodiment, the at least one resin chosen from hydrocarbon-bases resins is formulated by dissolving a thermoplastic polyolefin in accordance with the invention, such as C5PO, in isododecane or a light paraffinic solvent. In another preferred embodiment, the hydrocarbon-based resins may be formulated by dissolving the C5PO in a non-hydrocarbon solvent such as amyl acetate, butyl acetate, isobutyl acetate, ethyl acetate, propyl acetate or isopropyl acetate.

In the composition of the present invention, the at least one resin chosen from hydrocarbon-based resins is preferably present in an amount of from about 0.1 to about 60 percent by weight, more preferably from about 1 to about 40 percent by weight, and even more preferably from about 2 to about 20 percent by weight of the total weight of the composition, including all ranges and subranges therebetween.

Hyperbranched Polyol Compound

According to the present invention, compositions comprising at least one hyperbranched polyol compound are provided.

The at least one hyperbranched polyol compound of the present invention has at least two hydroxyl groups.

Preferably, the hyperbranched polyol has a hydroxyl number of at least 15, more preferably of at least 50, more preferably of at least 100, and more preferably of at least about 150. "Hydroxyl number" or "hydroxyl value" which is sometimes also referred to as "acetyl value" is a number which indicates the extent to which a substance may be acetylated; it is the number of milligrams of potassium hydroxide required for neutralization of the acetic acid liberated on saponifying 1 g of acetylated sample.

In accordance with the present invention, "hyperbranched polyol" refers to dendrimers, hyperbranched macromolecules and other dendron-based architectures. Hyperbranched polyols can generally be described as three-dimensional highly branched molecules having a tree-like structure. They are characterized by a great number of end groups, at least two of which are hydroxyl groups. The dendritic or "tree-like" structure preferably shows regular symmetric branching from a central multifunctional core molecule leading to a compact globular or quasi-globular structure with a large number of end groups per molecule. Suitable examples of hyperbranched polyols can be found in U.S. Pat. No. 7,423,104, and U.S. patent applications 2008/0207871 and 2008/0286152, the entire contents of all of which are hereby incorporated by reference.

Other suitable examples include alcohol functional olefinic polymers such as those available from New Phase Technologies.

For example, olefinic polymers such as those disclosed in U.S. Pat. No. 7,314,904, the entire content of which is hereby incorporated by reference, can be used. Thus, for example, a functionalized polyalphaolefin comprising the reaction product of admixing an alpha-olefin monomer having at least 10 carbon atoms and an unsaturated functionalizing compound can be used. Non-functionalized olefins that may be used in accordance with the present invention include, but are not limited to, 1-decene, 1-dodecene, 1-tetradecene, 1-hexadecene, 1-octadecene, 1-eicosene, as well as such commercial mixtures sold as alpha-olefins including those having mainly C10-C13, C20-C24 chain lengths, C24-C28 chain lengths and C30 and higher chain lengths. Examples of commercial alpha olefin admixtures useful with the present invention include ALPHA OLEFIN 30+ from Chevron Phillips and Alpha Olefin Fraction C30+ from Gulf.

Unsaturated functionalizing compounds useful with the present invention include, but are not limited to, carboxylic acids, carboxylic acid esters, amides, ethers, amines, phosphate esters, silanes and alcohols. Examples of such carboxylic acids include, but are not limited to, 5-hexenoic acid, 6-heptenoic acid, 10-undecylenic acid, 9-decenoic acid, oleic acid, and erucic acid. Also useful are esters of these acids with linear or branched-chain alcohols having from about 1 to about 10 carbon atoms, as well as triglycerides containing olefinic unsaturation in the fatty acid portion such as tall oil, fish oils, soybean oil, linseed oil, cottonseed oil and partially hydrogenated products of such oils. Other useful materials include olefinic alcohols such as allyl alcohol, 9-decen-1-ol, 10-undecylenyl alcohol, oleyl alcohol, erucyl alcohol, acetic acid or formic acid esters of these alcohols, C1-C4 alkyl ether derivatives of these alcohols and formamides or acetamides of unsaturated amines such as oleylamine, erucylamine, 10-undecylenylamine and allylamine.

The molar ratio of alpha olefin monomer to unsaturated functionalizing compound useful with the present invention is preferably from about 20:1 to 1:20. Also preferably, the molar ratio of alpha olefin monomer to unsaturated functionalizing compound useful with the present invention is from about 10:1 to 1:10. Most preferably the molar ratio of alpha olefin monomer to unsaturated functionalizing compound useful with the present invention is from about 8:1 to 1:2.

After the polymerization, the functionalized polyalphaolefins of the present invention preferably have a molecular weight, determined using gel permeation chromatography procedure and a polystyrene standard of from about 200 daltons to about 150,000 daltons. Also preferably, the functionalized polyalphaolefins of the present invention have a molecular weight of from about 400 daltons to about 80,000 daltons. Most preferably, the functionalized polyalphaolefins of the present invention have a molecular weight of from about 600 daltons to about 6,000 daltons.

According to preferred embodiments, the alcohol functional olefinic polymer has a dynamic viscosity preferably ranging from 0.1 Pa·s to 100 Pa·s, preferably ranging from 0.1 Pa·s to 50 Pa·s, and preferably ranging from 0.1 Pa·s to 10 Pa·s at room temperature.

A particularly preferred alcohol functional olefinic polymer is C20-C24 olefin/oleyl alcohol available from New Phase Technologies.

With respect to dendrimers, these tend to be exact, monodisperse structures built layerwise (in generations) around a core moiety, with a polymer branching point in every repeating unit. Hyperbranched polymers tend to possess a number of characteristics which are similar to dendrimers but they tend to be polydisperse and contain relatively linear segments off of which a plurality of highly branched segments are grown or attached.

Furthermore, "hyperbranched polymers" refers to polymers comprising at least two, for example three, polymeric branches, forming either the main branch or a secondary branch, and each comprising at least one at least trifunctional branch point, which may be identical or different, and which is able to form at least two at least trifunctional branch points, different from and independent of one another. Each branch point may be, for example, arranged in the interior of at least one chain. The branches may be, for example, connected to one another by a polyfunctional compound.

As used herein, "trifunctional branch point" means the junction point between three polymer branches, of which at least two branches may be different in chemical constitution and/or structure. For example, certain branches may be hydrophilic, i.e. may predominantly contain hydrophilic monomers, and other branches may be hydrophobic, i.e., may predominantly contain hydrophobic monomers. Further branches may additionally form a random polymer or a block polymer.

As used herein, "at least trifunctional branch" means the junction points between at least three polymeric branches, for example n polymeric branches, of which n−1 branches at least are different in chemical constitution and/or structure.

As used herein, "chain interior" means the atoms situated within the polymeric chain, to the exclusion of the atoms forming the two ends of this chain.

As used herein, "main branch" means the branch or polymeric sequence comprising the greatest percentage by weight of monomer(s).

Branches which are not main branches are called "secondary branches".

According to particularly preferred embodiments of the present invention, the hyperbranched polyol comprises a hydrophobic chain interior. Preferably, the chain interior comprises one or more hydrocarbon groups, one or more silicon-based groups, or mixtures thereof. Particularly preferred chain interiors comprise olefinic polymers or copolymers and/or silicone polymers or copolymers.

Suitable olefinic monomers include, but are not limited to, compounds having from about 2 to about 30 carbon atoms per molecule and having at least one olefinic double bond which are acyclic, cyclic, polycyclic, terminal α, internal, linear, branched, substituted, unsubstituted, functionalized, and/or non-functionalized. For example, suitable monomers include ethylene, propylene, 1-butene, 2-butene, 3-methyl-1-butene, and isobutylene.

Suitable silicone groups for inclusion into the interior chain include, but are not limited to, M, D, T, and/or Q groups in accordance with commonly used silicon-related terminology (M=monovalent; D=divalent; T=trivalent; and Q=quadvalent). Particularly preferred monomers are "D" groups such as dimethicone or substituted dimethicone groups. Such groups can help form, for example, suitable dimethicone copolyols in accordance with the present invention.

A particularly preferred at least one hyperbranched polyol compound for use in the present invention is chosen from an alcohol functional olefinic polymer such as C20-C24 olefin/oleyl alcohol, commercially available from New Phase Technologies.

According to preferred embodiments, the at least one hyperbranched polyol is present in the composition of the present invention in an amount ranging from about 0.5 to about 25% by weight, preferably from about 1 to about 20% by weight, more preferably from about 1.5 to about 15% by weight, even more preferably, from about 2 to about 10% by weight, from based on the total weight of the composition, including all ranges and subranges within these ranges.

Non-Volatile Solvent

According to the present invention, compositions comprising at least one non-volatile solvent chosen from monoalcohols are provided. The at least one non-volatile solvent chosen from monoalcohols is employed in the compositions of the present invention in order to solubilize the above-described polyester of the present invention.

Examples of suitable non-volatile solvent chosen from monoalcohols, include, but are not limited to, fatty alcohols. By nonvolatile what is meant is they have a boiling point at 1.0 atmospheres of at least about 260 degrees C., preferably at least about 275 degrees C., more preferably at least about 300 degrees C.

Preferably, the fatty alcohols suitable for use in composition of the present invention have a low melting point such as a melting point of 30 degrees C. or less, preferably about 25 degrees C. or less, more preferably about 22 degrees C. or less. Suitable fatty alcohols include unsaturated monohydric straight chain fatty alcohols, saturated branched chain fatty alcohols, saturated C8-C12 straight chain fatty alcohols, and mixtures thereof. The unsaturated straight chain fatty alcohols will typically have one degree of unsaturation. Di- and tri-unsaturated alkenyl chains may be present at low levels, preferably less than about 5 percent by total weight of the unsaturated straight chain fatty alcohol more preferably less than about 2 percent, most preferably less than about 1 percent. Preferably, the unsaturated straight chain fatty alcohols will have an aliphatic chain size of from C12-C22, more preferably from C12-C18, most preferably from C16-C18. Exemplary alcohols of this type include oleyl alcohol, and palmitoleic alcohol. The branched chain alcohols will typically have aliphatic chain sizes of from C12-C22, preferably C14-C20, more preferably C16-C18.

Exemplary branched chain alcohols for use herein include stearyl alcohol, cetyl alcohol, isostearyl alcohol, octyldodecanol, and octyldecanol.

Examples of saturated C8-C12 straight chain alcohols include octyl alcohol, caprylic alcohol, decyl alcohol, and lauryl alcohol.

Particularly preferred non-volatile solvents chosen from monoalcohols for use in the present invention are chosen from isostearyl alcohol, octyldodecanol and mixtures thereof.

According to preferred embodiments, the at least one non-volatile solvent chosen from monoalcohols is present in the composition of the present invention in an amount ranging from about 1 to about 30% by weight, preferably from about 5 to about 27% by weight, more preferably from about 10 to about 25% by weight, based on the total weight of the composition, including all ranges and subranges within these ranges.

Co-Solvent

According to the present invention, compositions comprising at least one co-solvent chosen from esters are provided.

Examples of the at least one co-solvent chosen from esters in the present invention include, but are not limited to, fatty acid esters of glycerol such as those contained in hydrocarbon-based plant oils with a high triglyceride content and wherein the fatty acids may have varied chain lengths, these chains possibly being linear or branched, and saturated or unsaturated. Examples of such oils are wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, which is for instance sold by the company Stearineries Dubois or under the trade names Miglyol 810, 812 and 818 by the company Dynamit Nobel.

Other examples of esters suitable as co-solvents in the present invention are linear fatty acid esters having a total carbon number ranging from 30 to 100, such as pentaerythrityl tetrapelargonate (MM=697.05 g/mol); hydroxy esters, such as diisostearyl malate (MM=639 g/mol); aromatic esters such as tridecyl trimellitate (MM=757.19 g/mol); esters of C24-C28 branched fatty acids or fatty alcohols, such as those described in EP-A-0 955 039, for example triisocetyl citrate (MM=856 g/mol), pentaerythrityl tetraisononanoate (MW=697.05 g/mol), glyceryl triisostearate (MW=891.51 g/mol), glyceryl 2-tridecyltetradecanoate (MW=1143.98 g/mol), pentaerythrityl tetraisostearate (MW=1202.02 g/mol), poly-2-glyceryl tetraisostearate (MW-1232.04 g/mol) and pentaerythrityl 2-tetradecyltetradecanoate (MW=1538.66 g/mol); octyldodecyl/PPG-3 myristyl ether dimer dilinoleate (MW=1210 g/mol); and mixtures thereof. Suitable ester oils can also be described according to formula $R_1COOR_2$ in which $R_1$ represents a linear or branched higher fatty acid residue containing from 1 to 40 carbon atoms, including from 7 to 19 carbon atoms, and $R_2$ represents a branched hydrocarbon-based chain containing from 1 to 40 carbon atoms, including from 3 to 20 carbon atoms, with $R_1+R_2$ ☐ 10, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters.

Particularly preferred co-solvents chosen from esters for use in the present invention, include C12-C15 alkyl benzoate, octyldodecyl/PPG-3 myristyl ether dimer dilinoleate, bisdiglyceryl polyacyladipate-2, bis-behenyl/isostearyl/phytosteryl dimer dilinoleyl dimer dilinoleate, caprylic/capric triglycerides, and mixtures thereof.

According to preferred embodiments, the at least one co-solvent chosen from esters is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

Wax

According to preferred embodiments of the present invention, the compositions of the present invention may comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline, wax, ceresin or ozokerite, palm kernel glycerides/hydrogenated palm glycerides and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

If present, the wax or waxes may be present in an amount ranging from 0.1 to 50% by weight relative to the total weight of the composition, for example from 1 to 30%, and for example from 3 to 25%, based on the total weight of the composition, including all ranges and subranges therebetween.

Colorants

According to preferred embodiments of the present invention, compositions further comprising at least one colorant are provided. Preferably, such colored compositions can be cosmetic compositions such as, for example, lip compositions (for example, lipstick or liquid lip colors or lip gloss), mascaras, eyeshadow, nail polish or foundations.

According to this embodiment, the at least one colorant is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Film-Forming Polymer

According to preferred embodiments of the present invention, the compositions may comprise at least one additional film-forming polymer.

In the present invention, the term "film-forming polymer" means a polymer that is capable, by itself or in the presence of an auxiliary film-forming agent, of forming a macroscopically continuous deposit on keratin materials. The composition may comprise an aqueous phase, and the film-forming polymer may be present in this aqueous phase. In this case, it will preferably be a polymer in dispersion or an amphiphilic or associative polymer.

The term "polymer in dispersion" means water-insoluble polymers present in the form of particles of variable size. The polymer may or may not be crosslinked. The size of the polymer particles is typically between 25 and 500 nanometers and preferably between 50 and 200 nanometers. The following polymers in aqueous dispersion may be used: Ultrasol 2075 from Ganz Chemical, Daitosol 5000 AD from Daito Kasei, Avalure UR 450 from Noveon, DynamX from National Starch, Syntran 5760 from Interpolymer, Acusol OP 301 from Röhm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Soltex OPT by the company Röhm & Haas, aqueous dispersions of acrylic or styrene/acrylic polymers sold under the brand name Joncryl® by the company Johnson Polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Röhm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

The composition may comprise an oily phase and the film-forming polymer may be present in this oily phase. The polymer may then be in dispersion or in solution.

As examples of lipodispersible non-aqueous film-forming polymer dispersions in the form of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may especially be vinyl polymers or copolymers, especially acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group that may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof.

The vinyl film-forming polymers may also result from the homopolymerization or copolymerization of monomers chosen from vinyl esters and styrene monomers.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and α-methylstyrene.

Among the film-forming polycondensates that may be mentioned are polyurethanes, polyesteramides, polyamides, epoxyester resins, polyureas and polyesters.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

According to one example of a composition according to the invention, the film-forming polymer may be a polymer dissolved in a liquid fatty phase comprising organic solvents or oils (the film-forming polymer is thus said to be a liposoluble polymer). The liquid fatty phase preferably comprises a volatile oil, optionally mixed with a non-volatile oil.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an α-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly (meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of C2-C20 alkenes, such as polybutene, alkylcelluloses with a linear or branched, saturated or unsaturated C1-C8 alkyl radical, for instance ethylcellulose and propylcellulose.

The composition according to the invention may comprise a plasticizer that promotes the formation of a film with the film-forming polymer. Such a plasticizer may be chosen from any compound known to those skilled in the art as being capable of fulfilling the desired function.

A preferred at least one film forming polymer for use in the compositions of the present invention is chosen from copolymers of vinyl acetate and copolymers of vinylpyrrolidone such as allyl stearate/vinyl acetate copolymer, commercially available from Chimex under the trade name Mexomere PQ®, VP/hexadecene copolymer, commercially available from International Specialty Products (ISP) under the trade names Antaron® V 216 or Ganex® V 216, and VP/eicosene copolymer, commercially available from ISP under the trade names Antaron® V 220 or Ganex® V 220.

The at least one film-forming polymer may be present in the composition of the present invention in an amount ranging from about 0.1% to about 30% by weight; such as from about 0.5% to about 20% by weight; such as from about 1% to about 10% by weight based on the total weight of the composition, including all ranges and subranges therebetween.

Volatile Solvent

In the event that at least one film-forming polymer as described above is present, the compositions of the present invention comprise at least one volatile solvent.

The expression "volatile solvent" means any non-aqueous medium capable of evaporating on contact with the skin or the lips in less than one hour at room temperature and atmospheric pressure.

Examples of suitable volatile solvents include, but are not limited to, volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3St) from Dow Corning | 102 | 3 |

The at least one volatile solvent is generally present in the composition of the present invention in an amount ranging from about 1% to about 50% by weight; such as from about 2% to about 40% by weight; such as from about 3% to about 20% by weight, all weights being based on the weight of the composition as a whole.

Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, plant extracts, amino acids, skin active agents, pasty compounds, viscosity increasing agents, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the skin, lips, hair and eyelashes of human beings.

According to preferred embodiments of the present invention, the compositions of the present invention are anhydrous. By "anhydrous," it is meant that the composition contains substantially no water (that is, less than about 5% by weight of the composition of water).

In other preferred embodiments of the present invention, the compositions of the present invention are substantially free of silicone oils or silicone resins or silicone fluids (i.e., contain less than about 0.5% silicone oils or silicone resins or silicone fluids).

Another particularly preferred embodiment of the present invention is a composition which contains so little elastomer that the presence of such elastomer does not affect the cosmetic properties of the composition. Preferably, the compositions are substantially free of such elastomers (i.e., contain less than about 0.5% elastomer), essentially free of such elastomers (i.e., contain less than about 0.25% elastomer) or free of such elastomer (i.e., contain no elastomer).

According to other embodiments, the compositions of the present invention may contain water. In the event that the composition of the present invention includes water, the compositions of the present invention can comprise water in an amount of from about 1% to about 30% water, more preferably from about 5% to about 25% water, and more preferably from about 10% to about 20% water by weight with respect to the total weight of the composition, including all ranges and subranges therebetween.

According to preferred embodiments of the present invention, methods of making up keratinous substrates such as skin, lips, eyes, hair and eyelashes by applying compositions of the present invention to the keratinous substrates in an amount sufficient to make up the keratinous substrates are provided. Preferably, "making up" the keratinous substrates includes applying the compositions of the present invention comprising at least one colorant to the keratinous substrate in an amount sufficient to provide color to the keratinous substrate.

According to yet other preferred embodiments, methods of enhancing the appearance of keratinous substrates by applying compositions of the present invention to the keratinous substrates in an amount sufficient to enhance the appearance of keratinous substrates are provided.

In accordance with the preceding preferred embodiments, the compositions of the present invention comprising at least one polyester as described in the present invention, at least one resin chosen from hydrocarbon-based resins, at least one hyperbranched polyol compound, at least one non-volatile solvent chosen from monoalcohols, at least one co-solvent chosen from esters, optionally, at least one wax, and optionally, at least one colorant are applied topically to the desired area of the keratinous substrate in an amount sufficient to make up the keratinous material, to cover or hide defects associated with keratinous substrates, skin imperfections or discolorations, or to enhance the appearance of the keratinous substrate. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

It has been surprisingly discovered that the composition of the present invention has improved cosmetic properties such as long wear, high shine and long-lasting shine, improved feel upon application and at the same time, comfort, a non-tacky feel and minimal feathering and migration disadvantages.

It has also been surprisingly discovered that the association of a polyester as described in the present invention, at least one resin chosen from hydrocarbon-based resins, a hyperbranched polyol compound, a non-volatile solvent chosen from monoalcohols, and a co-solvent chosen from esters results in the formation of a composition having long wear, high shine, long-lasting shine, comfort, good film deposit and texture characteristics as well as a non-tacky and a smooth/creamy feel when applied onto a keratinous substrate. Moreover, lipstick formulas of the above-described compositions surprisingly exhibited minimal feathering and migration disadvantages.

The compositions of the present invention are useful as compositions for making up and/or enhancing the appearance of the skin. These compositions include lipstick, lip gloss, eyeshadow, foundation and mascara products in the form of a solid, a semi-solid or a cream.

The compositions of the present invention are also useful as compositions for enhancing the appearance of hair. These compositions include hair styling and grooming products.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Correct Formulation Examples are Show Below

Example 1

Inventive Lipstick Formulations

| Ingredient | A | B | C | D |
|---|---|---|---|---|
| Polyester: benzoic acid/isophthalic acid/isotearic acid/pentaerythritol polyester | 12 | 10 | 6 | 3 |
| Hydrogenated styrene/methyl styrene/indene copolymer | 12 | 12 | 12 | 12 |
| C20-24 Olefin/oleyl alcohol copolymer | 10 | 10 | 10 | 10 |
| Bis-diglyceryl polyacryl adipate-2 | — | 2.0 | 6.0 | 9.0 |
| Isohexadecane | 3.0 | 3.0 | 3.0 | 3.0 |
| Isostearyl alcohol | 3.0 | 3.0 | 3.0 | 3.0 |
| Octyldodecanol | 6.5 | 6.5 | 6.5 | 6.5 |
| C12-15 alkyl benzoate | 12.3 | 12.3 | 12.3 | 12.3 |
| Octyldodecyl/PPG-3 myristyl ether dimer dilinoleate | 9.0 | 9.0 | 9.0 | 9.0 |
| Polyvinyl Laurate | 4.0 | 4.0 | 4.0 | 4.0 |
| Allyl stearate VA copolymer | 1.5 | 1.5 | 1.5 | 1.5 |
| VP-eicosene copolymer | 3.0 | 3.0 | 3.0 | 3.0 |
| Hydrogenated palm kernel glycerides/hydrogenated palm glycerides | 5.0 | 5.0 | 5.0 | 5.0 |
| Jojoba wax flakes | 2.2 | 2.2 | 2.2 | 2.2 |
| Polyethylene | 5.5 | 5.5 | 5.5 | 5.5 |
| Silica | 1.0 | 1.0 | 1.0 | 1.0 |
| Pigments/Pearls | 7.0 | 7.0 | 7.0 | 7.0 |
| Mica | 3.0 | 3.0 | 3.0 | 3.0 |
| Stick hardness (gram-force) | 112 | 121 | 125 | 138 |
| Visual observation of shine on lips | Good shine | Good shine | Good shine | Less shine |

Example 2

Comparative Formulations

| Ingredient | E Inventive formula | G Comparative formula |
|---|---|---|
| Polyester: benzoic acid/isophthalic acid/isotearic acid/pentaerythritol polyester | 8.0 | — |
| Hydrogenated styrene/methyl styrene/indene copolymer | 12 | 12 |
| C20-24 Olefin/oleyl alcohol copolymer | 10 | 10 |
| Bis-diglyceryl polyacryl adipate-2 | — | 12 |
| Isohexadecane | 3.0 | 3.0 |
| Isostearyl alcohol | 3.0 | 3.0 |
| Octyldodecanol | 6.5 | 6.5 |
| C12-15 alkyl benzoate | 12.3 | 12.3 |
| Octyldodecyl/PPG-3myristyl ether dimer dilinoleate | 9.0 | 9.0 |
| Polyvinyl Laurate | 4.0 | 4 |
| Allyl stearate VA copolymer | 1.5 | 1.5 |
| VP-eicosene copolymer | 3.0 | 3.0 |
| Hydrogenated palm kernel glycerides/hydrogenated palm glycerides | 5.0 | 5.0 |
| Jojoba wax flakes | 2.2 | 2.2 |
| Polyethylene | 5.5 | 5.5 |
| Silica | 1.0 | 1.0 |
| Pigments/Pearls | 7.0 | 7.0 |
| Mica | 7.0 | 3.0 |
| Shine evaluation | 145.9 ± 12.3 | 151.6 ± 10.2 |
| Shine evaluation over 1 h | 131.9 ± 16.6 | 143.1 ± 19.6 |
| Shine evaluation over 2 h | 119.5 ± 20.0 | 130.9 ± 24.5 |
| Migration 2 h | 0.2 ± 0.3 | 1.1 ± 0.5 |

The formulation examples above were tested on lips for shine, upon application and after one hour and two houses, and for migration/feathering of the lipstick on the lips.

Wear of color, shine, and feathering/migration were measured by a camera and a polarimetric SAMBA Chromasphère LFC-804-SBWA. See also FR 2829344.

The wear of a cosmetic composition reflects its ability to withstand the mechanical or physical stress, such as rubbing or stretching of the surface makeup.

The wear of a composition of the invention can be assessed by different protocols, such as described below.

Evaluation of wear of color is performed as follows: the holding is assessed after a series of standardized tests (consisting in two "kisses" on a paper towel, making a warm drink and a cold drink and/or hot, and making a small standardized meal, such as eating two bites of a sandwich and an apple).

Shine is measured just after application of the formula and then one hour after application, and/or 2 hours after application.

Migration is assessed one hour after application scoring.

The formulations are applied to the lips of a panel of six subjects with thick lips and clear.

The results above show that, the inventive formulas demonstrated long wear of color, high and long-lasting shine, even in the absence of silicones in the formula, and minimal migration/feathering of the lipstick on the lips. At the same time, the inventive formulas provided a thick film deposit, a good comfort level, a non-tacky feel and a smooth/creamy feel on the wearer's lips. They were also found to have good glide properties during application onto the lips. On the other hand, comparative formula G, this formula provided a non-tacky feel on the lips and good glide properties during application; however, it imparted only a moderate amount of shine on the lips with significant migration/feathering.

Method of making:
Procedure for Phase I:
Hydrogenated polydecene, trimethyl pentaphenyl trisiloxane, and hydrogentate styrene/butadiene copolymer were mixed, and the mixture was heated to 100° C. while mixing. Hydrogenated styrene/methyl styrene/indene copolymer was slowly added and mixing was continued until homogeneous on lowest speed.

Procedure for Pigment Grind:

The pigments were combined with a portion of Phase I and ground in a discontimill grinder.

The waxes, pigment grind, and other ingredients were combined with Phase I and mixed at 99° C. until the resulting mixture was homogeneous. The mixture was slightly cooled and then poured and chilled to form the stick.

It is to be understood that the foregoing describes preferred embodiments of the invention and that modifications may be made therein without departing from the spirit or scope of the invention as set forth in the claims.

What is claimed is:

1. A cosmetic composition comprising:
   (a) a polyester obtained by reacting:
      from about 10% to about 30% of a tetraol containing from 4 to 10 carbon atoms;
      from about 40% to about 80% of a linear or branched saturated monocarboxylic acid containing from 9 to 23 carbon atoms;
      from about 5% to about 30% of a cyclic dicarboxylic acid containing from 6 to 12 carbon atoms; and
      from about 1.0% to about 10% of an aromatic monocarboxylic acid containing from 7 to 11 carbon atoms; the above weights being based on the total weight of the polyester, said polyester having a weight-average molecular mass from about 3,000 g/ml to about 1,000,000, and a viscosity measured at 110° C. of between about 20 and about 4000 mPa*s, and being present in an amount from about 1% to about 20% by weight of the final composition;
   (b) at least one resin chosen from hydrocarbon-based resins, said resin comprising from about 1% to about 40% by weight of the final composition;
   (c) at least one hyperbranched polyol compound, said hyperbranched polyol comprising from about 1.0% to about 20% by weight of the final composition;
   (d) at least one non-volatile solvent chosen from monoalcohols, said solvent comprising from about 5% to about 27% by weight of the final composition;
   (e) at least one co-solvent chosen from esters, said co-solvent comprising from about 10% to about 50% by weight of the final composition;
   (g) optionally, at least one wax, which when present comprises from about 0.1% to about 50% by weight of the final composition; and
   (h) optionally, at least one colorant,
said composition being substantially free of silicone oil.

2. The composition of claim 1, wherein component(a) is obtained by reacting:
   from about 12% to about 25% by weight of a tetraol containing from 4 to 10 carbon atoms, based on the total weight of the polyester;
   from about 50% to about 65% by weight of a linear or branched saturated monocarboxylic acid containing from 9 to 23 carbon atoms, based on the total weight of the polyester;
   from about 15% to about 25% by weight of a cyclic dicarboxylic acid containing from 6 to 12 carbon atoms, based on the total weight of the polyester; and
   from about 1.0% to about 9.5% by weight of an aromatic monocarboxylic acid containing from 7 to 11 carbon atoms, based on the total weight of the polyester.

3. The composition of claim 2, wherein the tetraol containing from 4 to 10 carbon atoms is chosen from diglycerol and pentaerythritol.

4. The composition of claim 3, wherein the linear or branched saturated monocarboxylic acid containing from 9 to 23 carbon atoms is chosen from stearic acid and isostearic acid.

5. The composition of claim 4, wherein the cyclic dicarboxylic acid containing from 6 to 12 carbon atoms is isophthalic acid.

6. The composition of claim 5, wherein the aromatic monocarboxylic acid containing from 7 to 11 carbon atoms is chosen from benzoic acid and 4-tert-butylbenzoic acid.

7. The composition of claim 2, wherein (a) is chosen from benzoic acid/isophthalic acid/isostearic acid/pentaerythritol polyesters, benzoic acid/isophthalic acid/stearic acid/pentaerythritol polyesters, and mixtures thereof.

8. The composition of claim 7, wherein (b) has an average molecular weight of less than or equal to 5000.

9. The composition of claim 8, wherein (b) is chosen from indene resins, aliphatic pentanediene resins, mixed resins of pentanediene and of indene, diene resins of cyclopentadiene dimers and diene resins of isoprene dimers, and mixtures thereof.

10. The composition of claim 9, wherein (b) is chosen from hydrogenated styrene/methyl styrene/indene copolymers.

11. The composition of claim 8, wherein (c) is an alcohol functional olefinic polymer.

12. The composition of claim 11, wherein (c) is C20-C24 olefin/oleyl alcohol copolymer.

13. The composition of claim 12, wherein (d) is chosen from isostearyl alcohol, octyldodecanol and mixtures thereof.

14. The composition of claim 13, wherein (e) is chosen from C12-C15 alkyl benzoate, octyldodecyl/PPG-3 myristyl ether dimer dilinoleate, bis-diglyceryl polyacyladipate-2, bis-behenyl/isostearyl/phytosteryl dimer dilinoleyl dimer dilinoleate, caprylic/capric triglycerides, and mixtures thereof.

15. The composition of claim 2, wherein the composition is a lipstick comprising at least one colorant.

16. A method of making up and/or enhancing the appearance of a keratinous substrate comprising applying onto the keratinous substrate a cosmetic composition containing:
   (a) at least one polyester obtained by reacting:
      a tetraol containing from 4 to 10 carbon atoms;
      a linear or branched saturated monocarboxylic acid containing from 9 to 23 carbon atoms;
      a cyclic dicarboxylic acid containing from 6 to 12 carbon atoms; and
      an aromatic monocarboxylic acid containing from 7 to 11 carbon atoms;
   (b) at least one resin chosen from hydrocarbon-based resins;
   (c) at least one hyperbranched polyol compound;
   (d) at least one non-volatile solvent chosen from monoalcohols;
   (e) at least one co-solvent chosen from esters;
   (f) at least one nonvolatile silicone oil;
   (g) optionally, at least one wax; and
   (h) optionally, at least one colorant,
wherein the content of the silicone oil is less than or equal to 10% by weight based on the total weight of the composition.

17. The method of claim 16, wherein (a) is obtained by reacting:
   from 10% to 30% by weight of a tetraol containing from 4 to 10 carbon atoms, based on the total weight of the polyester;

from 40% to 80% by weight of a linear or branched saturated monocarboxylic acid containing from 9 to 23 carbon atoms, based on the total weight of the polyester;

from 5% to 30% by weight of a cyclic dicarboxylic acid containing from 6 to 12 carbon atoms, based on the total weight of the polyester; and from 0.1% to 10% by weight of an aromatic monocarboxylic acid containing from 7 to 11 carbon atoms, based on the total weight of the polyester.

18. The method of claim 16, wherein the tetraol containing from 4 to 10 carbon atoms is chosen from diglycerol and pentaerythritol.

19. The method of claim 16, wherein the linear or branched saturated monocarboxylic acid containing from 9 to 23 carbon atoms is chosen from stearic acid and isostearic acid.

20. The method of claim 16, wherein the cyclic dicarboxylic acid containing from 6 to 12 carbon atoms is isophthalic acid.

21. The method of claim 16, wherein the aromatic monocarboxylic acid containing from 7 to 11 carbon atoms is chosen from benzoic acid and 4-tert-butylbenzoic acid.

22. The method of claim 16, wherein (a) is chosen from benzoic acid/isophthalic acid/isostearic acid/pentaerythritol polyesters, benzoic acid/isophthalic acid/stearic acid/pentaerythritol polyesters, and mixtures thereof.

23. The method of claim 16, wherein (a) is present in the composition in an amount of from about 0.5 to about 25% by weight, based on the total weight of the composition.

24. The method of claim 16, wherein (b) has an average molecular weight of less than or equal to 5000.

25. The method of claim 16, wherein (b) is chosen from indene resins, aliphatic pentanediene resins, mixed resins of pentanediene and of indene, diene resins of cyclopentadiene dimers and diene resins of isoprene dimers, and mixtures thereof.

26. The method of claim 16, wherein (b) is chosen from hydrogenated styrene/methyl styrene/indene copolymers.

27. The method of claim 16, wherein (b) is present in the composition in an amount of from about 0.1 to about 60% by weight, based on the total weight of the composition.

28. The method of claim 16, wherein (c) is a hyperbranched alcohol functional olefinic polymer.

29. The method of claim 16, wherein (c) is C20-C24 olefin/oleyl alcohol copolymer.

30. The method of claim 16, wherein (c) is present in the composition in an amount of from about 1 to about 30% by weight, based on the total weight of the composition.

31. The method of claim 16, wherein (d) is chosen from isostearyl alcohol, octyldodecanol and mixtures thereof.

32. The method of claim 16, wherein (d) is present in the composition in an amount of from about 1 to about 30% by weight, based on the total weight of the composition.

33. The method of claim 16, wherein (e) is chosen from C12-C15 alkyl benzoate, octyldodecyl/PPG-3 myristyl ether dimer dilinoleate, bis-diglyceryl polyacyladipate-2, bis-behenyl/isostearyl/phytosteryl dimer dilinoleyl dimer dilinoleate, caprylic/capric triglycerides, and mixtures thereof.

34. The method of claim 16, wherein (e) is present in the composition in an amount of from about 5 to about 60% by weight, based on the total weight of the composition.

35. The method of claim 16, wherein (g) is present in the composition in an amount of from about 0.1 to about 50% by weight, based on the total weight of the composition.

36. The method of claim 16, wherein (h) is present in an amount effective to impart color when applied onto keratinous substrates.

37. A lipstick composition comprising:
  (a) from about 0.5% to about 25% by weight of at least one polyester obtained by reacting:
    from 10% to 30% by weight of pentaerythritol, based on the total weight of the polyester;
    from 40% to 80% by weight of isostearic acid, based on the total weight of the polyester;
    from 5% to 30% by weight of isophthalic acid, based on the total weight of the polyester; and
    from 1.0% to 10% by weight of benzoic acid, based on the total weight of the polyester;
    said polyester having a weight-average molecular mass from about 3,000 g/ml to about 1,000,000, and a viscosity measured at 110° C. of between about 20 and about 4000 mPa*s and being present in an amount from about 1% to about 20% by weight of the final composition;
  (b) from about 1.0% to about 40% by weight of a resin chosen from hydrocarbon-based resins;
  (c) from about 1% to about 20% by weight of a hyperbranched polyol compound;
  (d) from about 5% to about 27% by weight of a non-volatile solvent chosen from monoalcohols;
  (e) from about 5% to about 30% by weight of a co-solvent chosen from esters;
  (g) from about 1% to about 30% by weight of at least one wax; and
  (h) optionally, at least one colorant;
wherein the weights of (a)-(h) are based on the total weight of the composition; said composition being substantially free of silicone oil.

38. The composition of claim 37 wherein component (a) is benzoic acid/isophthalic acid/isostearic acid/pentaerythritol polyester.

39. The composition of claim 38 wherein component (b) is a hydrogenated styrene/methyl styrene/indene copolymer.

40. The composition of claim 39 wherein component (c) is $C_{20}$-$C_{24}$ olefin/oleyl alcohol copolymer.

41. The composition of claim 40 wherein component (d) is selected from isostearyl alcohol, octyldodecanol and mixtures thereof.

42. The composition of claim 41 wherein component (e) is selected from $C_{12}$-$C_{15}$ alkyl benzoate, octyldodecyl/PPG-3 myristyl ether dimer dilinoleate, bis-diglyceryl polyacyladipate-2, and mixtures thereof.

* * * * *